US008968769B2

(12) United States Patent
Bunick et al.

(10) Patent No.: US 8,968,769 B2
(45) Date of Patent: Mar. 3, 2015

(54) ORALLY DISINTEGRATIVE DOSAGE FORM

(75) Inventors: Frank Bunick, Randolph, NJ (US); Joseph Luber, Quakertown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 176 days.

(21) Appl. No.: 12/566,078

(22) Filed: Sep. 24, 2009

(65) Prior Publication Data
US 2010/0016451 A1    Jan. 21, 2010

Related U.S. Application Data

(63) Continuation of application No. 12/260,151, filed on Oct. 29, 2008, now abandoned.

(60) Provisional application No. 60/983,973, filed on Oct. 31, 2007.

(51) Int. Cl.
A61K 47/26 (2006.01)
A61K 47/10 (2006.01)
B29B 9/00 (2006.01)
A61K 9/00 (2006.01)
A61K 9/20 (2006.01)

(52) U.S. Cl.
CPC ............. *A61K 9/0056* (2013.01); *A61K 9/2009* (2013.01); *A61K 9/2018* (2013.01)
USPC ................ 424/440; 514/777; 514/772; 264/5

(58) Field of Classification Search
CPC .. A61K 9/0056; A61K 9/2009; A61K 9/2018
USPC .................... 424/440; 514/777, 772; 264/5
See application file for complete search history.

(56) References Cited

U.S. PATENT DOCUMENTS

| | | | |
|---|---|---|---|
| 2,183,053 A | 12/1939 | Taylor | |
| 2,887,437 A | 5/1959 | Klioze et al. | |
| 3,071,470 A | 1/1963 | Bishop | |
| 3,337,116 A | 8/1967 | Nowak | |
| 3,670,065 A | 6/1972 | Eriksson et al. | |
| 3,885,026 A | 5/1975 | Heinemann et al. | |
| 4,158,411 A | 6/1979 | Hall et al. | |
| 4,173,626 A | 11/1979 | Dempski et al. | |
| 4,230,693 A | 10/1980 | Izzo et al. | |
| 4,260,596 A | 4/1981 | Mackles | |
| 4,268,238 A | 5/1981 | Marc | |
| 4,268,465 A | 5/1981 | Suh et al. | |
| 4,327,076 A | 4/1982 | Puglia et al. | |
| 4,398,634 A | 8/1983 | McClosky | |
| 4,508,740 A | 4/1985 | McSweeney | |
| 4,526,525 A | 7/1985 | Oiso et al. |
| 4,590,075 A | 5/1986 | Wei et al. |
| 4,609,543 A | 9/1986 | Morris et al. |
| 4,642,903 A | 2/1987 | Davies |
| 4,684,534 A | 8/1987 | Valentine |
| 4,758,439 A | 7/1988 | Godfrey |
| 4,762,719 A | 8/1988 | Forester |
| 4,777,050 A | 10/1988 | Vadino |
| 4,824,681 A | 4/1989 | Schobel et al. |
| 4,828,845 A | 5/1989 | Zamudio-Tena et al. |
| 4,832,956 A | 5/1989 | Gergely et al. |
| 4,851,226 A | 7/1989 | Julian et al. |
| 4,857,331 A | 8/1989 | Shaw et al. |
| 4,863,742 A | 9/1989 | Panoz et al. |
| 4,906,478 A | 3/1990 | Valentine et al. |
| 4,979,720 A | 12/1990 | Robinson |
| 4,980,170 A | 12/1990 | Schneider et al. |
| 4,984,240 A | 1/1991 | Keren-Zvi et al. |
| 4,994,260 A | 2/1991 | Kallstrand et al. |
| 5,013,557 A | 5/1991 | Tai |
| 5,046,618 A | 9/1991 | Wood |
| 5,064,656 A | 11/1991 | Gergely et al. |
| 5,073,374 A | 12/1991 | McCarty |
| 5,075,114 A | 12/1991 | Roche |
| 5,082,436 A | 1/1992 | Choi et al. |
| 5,112,616 A | 5/1992 | McCarty |
| 5,126,151 A | 6/1992 | Bodor et al. |
| 5,134,260 A | 7/1992 | Piehler et al. |
| 5,139,407 A | 8/1992 | Kim et al. |
| 5,178,878 A | 1/1993 | Wehling et al. |
| 5,215,755 A | 6/1993 | Roche et al. |
| 5,223,264 A | 6/1993 | Wehling et al. |
| 5,262,171 A | 11/1993 | Login et al. |
| 5,275,822 A | 1/1994 | Valentine et al. |
| 5,286,497 A | 2/1994 | Hendrickson et al. |
| 5,304,055 A | 4/1994 | Van Lengerich et al. |

(Continued)

FOREIGN PATENT DOCUMENTS

CN    1141589 A    1/1997
CN    1498080 A    5/2004

(Continued)

OTHER PUBLICATIONS

Amin, Avani F., Emerging Trends in the Development of Orally Disintegrating Tablet Technology, Pharmainfo.net, vol. 4, Issue 1, Jan. 26, 2006; pp. 1-30.

(Continued)

*Primary Examiner* — Aradhana Sasan
(74) *Attorney, Agent, or Firm* — William E. McGowan

(57) ABSTRACT

The present invention features an orally disintegrating dosage form including from about 5% to about 40%, by weight, of at least one hydrated salt and a pharmaceutically active agent, wherein the at least one hydrated salt has a dehydration temperature of from about 20 to about 120 ° C.

17 Claims, No Drawings

(56) References Cited

U.S. PATENT DOCUMENTS

| | | | |
|---|---|---|---|
| 5,320,848 A | 6/1994 | Greyer et al. |
| 5,330,763 A | 7/1994 | Gole et al. |
| 5,464,632 A | 11/1995 | Cousin et al. |
| 5,489,436 A | 2/1996 | Hoy et al. |
| 5,501,858 A | 3/1996 | Fuisz |
| 5,501,861 A | 3/1996 | Makimo et al. |
| 5,503,846 A | 4/1996 | Wehling et al. |
| 5,558,880 A | 9/1996 | Gole et al. |
| 5,558,899 A | 9/1996 | Kuzee et al. |
| 5,560,963 A | 10/1996 | Tisack |
| 5,587,172 A | 12/1996 | Cherukuri et al. |
| 5,587,179 A | 12/1996 | Gergely et al. |
| 5,607,697 A | 3/1997 | Alkire et al. |
| 5,622,719 A | 4/1997 | Myers et al. |
| 5,631,023 A | 5/1997 | Kearney et al. |
| 5,635,210 A | 6/1997 | Allen, Jr. et al. |
| 5,648,093 A | 7/1997 | Gole et al. |
| 5,653,993 A | 8/1997 | Ghanta et al. |
| 5,662,849 A | 9/1997 | Bogne et al. |
| 5,672,364 A | 9/1997 | Kato et al. |
| 5,720,974 A | 2/1998 | Makino et al. |
| 5,814,339 A | 9/1998 | Prudhoe |
| 5,886,081 A | 3/1999 | Sternowski |
| 5,912,013 A | 6/1999 | Rudnic et al. |
| 5,939,091 A | 8/1999 | Eoga et al. |
| 5,997,905 A | 12/1999 | McTeigue et al. |
| 6,024,981 A | 2/2000 | Khankarti et al. |
| 6,060,078 A | 5/2000 | Lee |
| 6,103,260 A | 8/2000 | Luber et al. |
| 6,224,905 B1 | 5/2001 | Lawrence et al. |
| 6,228,398 B1 | 5/2001 | Devane et al. |
| 6,258,381 B1 | 7/2001 | Luber et al. |
| 6,270,805 B1 | 8/2001 | Chen et al. |
| 6,277,409 B1 | 8/2001 | Luber et al. |
| 6,284,270 B1 | 9/2001 | Lagoviyer et al. |
| 6,287,596 B1 | 9/2001 | Murakami et al. |
| 6,316,026 B1 | 11/2001 | Tatara et al. |
| 6,322,819 B1 | 11/2001 | Barnside et al. |
| 6,328,994 B1 | 12/2001 | Shimizu et al. |
| 6,465,010 B1 | 10/2002 | Lagoviyer et al. |
| 6,499,984 B1 | 12/2002 | Ghebre-Sellassie et al. |
| 6,569,463 B2 | 5/2003 | Patel et al. |
| 6,589,554 B1 | 7/2003 | Mizumoto et al. |
| 6,612,826 B1 | 9/2003 | Bauer et al. |
| 6,649,888 B2 | 11/2003 | Ryan et al. |
| 6,753,009 B2 | 6/2004 | Luber et al. |
| 6,767,200 B2* | 7/2004 | Sowden et al. | 425/345 |
| 6,814,978 B2 | 11/2004 | Bunick et al. |
| 6,932,979 B2 | 8/2005 | Gergely |
| 7,070,825 B2 | 7/2006 | Ndife et al. |
| 7,132,072 B2 | 11/2006 | Ozeki et al. |
| 7,157,100 B2 | 1/2007 | Doshi et al. |
| 7,625,622 B2 | 12/2009 | Teckoe et al. |
| 8,127,516 B2 | 3/2012 | Lee et al. |
| 8,313,768 B2 | 11/2012 | Kriksunov et al. |
| 2001/0033831 A1 | 10/2001 | Chow et al. |
| 2002/0012701 A1 | 1/2002 | Kolter et al. |
| 2002/0018800 A1 | 2/2002 | Pinney et al. |
| 2002/0079121 A1 | 6/2002 | Ryan et al. |
| 2002/0122822 A1* | 9/2002 | Bunick et al. | 424/464 |
| 2003/0021842 A1 | 1/2003 | Lagoviyer et al. |
| 2003/0068373 A1 | 4/2003 | Luber et al. |
| 2003/0161879 A1* | 8/2003 | Ohmori et al. | 424/465 |
| 2003/0175339 A1 | 9/2003 | Bunick et al. |
| 2003/0194442 A1 | 10/2003 | Guivarch et al. |
| 2003/0224044 A1* | 12/2003 | Weibel | 424/465 |
| 2003/0228368 A1 | 12/2003 | Wynn et al. |
| 2004/0115305 A1 | 6/2004 | Andersen et al. |
| 2004/0137057 A1 | 7/2004 | Sowden et al. |
| 2004/0156902 A1 | 8/2004 | Lee et al. |
| 2004/0191499 A1* | 9/2004 | Hallett et al. | 428/323 |
| 2005/0019407 A1 | 1/2005 | Sowden et al. |
| 2005/0138899 A1 | 6/2005 | Draisey et al. |
| 2005/0142188 A1 | 6/2005 | Gilis et al. |
| 2005/0186274 A1 | 8/2005 | Kohlrausch |
| 2006/0034927 A1* | 2/2006 | Casadevall et al. | 424/472 |
| 2006/0134195 A1 | 6/2006 | Fu et al. |
| 2007/0071806 A1 | 3/2007 | McCarty |
| 2007/0184111 A1 | 8/2007 | Harris et al. |
| 2007/0196477 A1 | 8/2007 | Witham et al. |
| 2007/0281009 A1 | 12/2007 | Kamisono et al. |
| 2008/0286340 A1 | 11/2008 | Andersson et al. |
| 2009/0060983 A1* | 3/2009 | Bunick et al. | 424/440 |
| 2009/0092672 A1 | 4/2009 | Venkatesh et al. |
| 2009/0110716 A1 | 4/2009 | Bunick et al. |
| 2009/0110717 A1 | 4/2009 | Singh et al. |
| 2011/0068511 A1 | 3/2011 | Sowden et al. |
| 2011/0071184 A1 | 3/2011 | Bunick et al. |

FOREIGN PATENT DOCUMENTS

| | | |
|---|---|---|
| CN | 101052373 A | 10/2007 |
| EP | 0 070 127 | 1/1983 |
| EP | 0192460 B1 | 8/1986 |
| EP | 0 416 791 A2 | 3/1991 |
| EP | 0829341 A2 | 3/1998 |
| EP | 1974724 A2 | 10/2008 |
| EP | 2308511 B1 | 12/2012 |
| GB | 772 315 A | 4/1957 |
| GB | 1 097 207 A | 12/1967 |
| GB | 1538280 A | 1/1979 |
| JP | 59 067006 A | 4/1984 |
| JP | 62/205009 A | 3/1986 |
| JP | 1999033084 A | 2/1999 |
| WO | WO 91/12881 | 9/1991 |
| WO | WO 92/06679 | 4/1992 |
| WO | WO 93/13758 | 7/1993 |
| WO | WO 94/06416 | 3/1994 |
| WO | WO 95/09044 A1 | 4/1995 |
| WO | WO 97/38679 A2 | 10/1997 |
| WO | WO 98/32426 A | 7/1998 |
| WO | WO 99/17771 | 4/1999 |
| WO | WO 99/44580 A | 9/1999 |
| WO | WO 00/04281 | 1/2000 |
| WO | WO 02/47607 | 6/2002 |
| WO | WO 03/059327 A1 | 7/2003 |
| WO | WO 03/061399 A1 | 7/2003 |
| WO | WO 03/101431 A1 | 12/2003 |
| WO | WO 04/000197 A | 12/2003 |
| WO | WO 2004/046296 A1 | 6/2004 |
| WO | WO 2004/100857 A2 | 11/2004 |
| WO | WO 2006/018074 A1 | 2/2006 |
| WO | WO 2006/127618 | 11/2006 |
| WO | WO 2007/042153 A | 4/2007 |
| WO | WO 2007/125545 A2 | 11/2007 |
| WO | WO 2007/141328 | 12/2007 |
| WO | WO 2008/005318 A2 | 1/2008 |
| WO | WO 2008/015221 A2 | 2/2008 |
| WO | WO 2009/037319 A2 | 3/2009 |
| WO | WO 2009/080022 A1 | 7/2009 |
| WO | WO 2010/058218 A1 | 5/2010 |
| WO | WO 2012/039788 A1 | 3/2012 |
| ZA | 8704899 | 3/1988 |

OTHER PUBLICATIONS

Matthes, R.; "Chapter 49" from website: http://www.ilo.org/safework_bookshelf/english?content&nd=857170571; made available online Oct. 12, 2004.

Google page showing the availability date of web reference U; provided Mar. 15, 2011.

Lieberman, Herbert A. et al., "Pharmaceutical Dosage Forms—Tablets", vol. 2, $2^{nd}$ Ed. pp. 213-217; 327-329, Marcel Dekker, Inc., 1990, New York and Basel.

Lachman, Leon et al., "The Theory and Practice of Industrial Pharmacy", $3^{rd}$ Ed., Chapter 11, pp. 293-345,Lea & Febiger, 1986, Philadelphia.

McConville, J. et al., "Erosion characteristics of an erodible tablet incorporated in a time-delayed capsule device," Drug Development and Industrial Pharmacy, vol. 31, No. 1, 2005, pp. 79-89, XP008108019.

USP 23 (1995) 1216, Tablet Friability, p. 1981.

(56) References Cited

OTHER PUBLICATIONS

USP 24, 2000 Version, Acetaminophen, pp. 19-20 and Ibuprofen, p. 856 (1999).
Orally Disintegrating Tablets, draft Food and Drug Administration Guidance, Apr. 2007.
Int'l. Search Report for Application No. PCT/US2008/081496, dated Jul. 15, 2009.
Int'l. Search Report for Application No. PCT/US2008/74375, dated Nov. 17, 2008.
Int'l. Search Report for Application No. PCT/US2010/049909 dated Dec. 3, 2010.
Int'l. Search Report for Application No. PCT/US2010/049925 dated Dec. 8, 2010.
Int'l. Search Report for Application No. PCT/US2010/049931 dated Jan. 7, 2011.
Int'l. Search Report for Application No. PCT/US2010/049933 dated Feb. 15, 2011.
Int'l. Search Report for Application No. PCT/US2010/049964 dated Dec. 30, 2010.
Int'l. Search Report for Application No. PCT/US2010/049971 dated Jan. 7, 2011.
U.S. Appl. No. 11/847,444, filed Aug. 30, 2007—Pending.
U.S. Appl. No. 12/570,046, filed Sep. 30, 2009—Pending.
U.S. Appl. No. 12/260,151, filed Oct. 29, 2008—Pending.
U.S. Appl. No. 12/566,078, filed Sep. 24, 2009—Pending.
U.S. Appl. No. 12/566,096, filed Sep. 24, 2009—Pending.
U.S. Appl. No. 12/887,544, filed Sep. 22, 2010—Pending.
U.S. Appl. No. 12/887,552, filed Sep. 22, 2010—Pending.
U.S. Appl. No. 12/887,560, filed Sep. 22, 2010—Pending.
U.S. Appl. No. 12/887,564, filed Sep. 22, 2010—Pending.
U.S. Appl. No. 12/887,569, filed Sep. 22, 2010—Pending.
U.S. Appl. No. 12/887,575, filed Sep. 22, 2010—Pending.
U.S. Appl. No. 12/887,582, filed Sep. 22, 2010—Pending.
U.S. Appl. No. 12/887,593, filed Sep. 22, 2010—Pending.
International Search Report dated Jul. 15, 2009 for PCT/US2008/081496.
International Search Report dated Nov. 17, 2008 for PCT/US2008/74375.
Heng, Paul Wan Sia, Chem Pharm Bull, 47 (5) 633-638 (1999).
Koral, Tony, Radio Frequency Heating and Post-Baking, Biscuit World, Issue 4, vol. 7, Nov. 2004.
Callebaut, Jean, Dielectric Heating, Leonardo Energy, Power Quality & Utilisation Guide, Section 7: Energy Efficiency, Mar. 2007; pp. 2-9.
Jones, P. L. et al, "Dielectric Drying", Drying Technology, 14(5), 1996, p. 1063-1098.
Guo, et al., Temperature and Moisture Dependent Dielectric Properties of Legume Flour Associated with Dielectric Heating, LWT Food Science and Technology 43, 2010, p. 193-201.
Katsuki, et al., Novel Energy-Saving Materials for Microwave Heating, Chem Mater. 2008, 20, p. 4803-4807.
Radio-Frequency Heating of Plastics, TechCommentary, vol. 4, No. 2, 1987, p. 1-4.
Jones, P. L., High Frequency Dielectric Heating in Paper Making, Drying Technology, 4(2), 1986, p. 217-244.
What is R.F. Heat Sealing?, Dielectric Sealing Service, Inc., 2007, p. 1-6.
Broadband RF Survey Instruments, ETS•LINDGREN Haladay EMF Measurement, 2002, p. 1-2.
Lamp IR Infrared Heaters: Infrared Lamps for Controlled Concentrated Heating, Research Inc., p. 1-20., Sep. 20, 2010.
Callebaut, Power Quality & Utilisation Guide, Section 7: Energy Efficiency, Mar. 2007, www.leonardo-energy.org, p. 1-9.
Shukla, et al., Mouth Dissolving Tablets I: An Overview of Formulation Technology, Sci Pharm 2009, 76: p. 309-326.
USP33—U.S. Pharmacopeia, General Chapter 701—Disintegration, 2008.
U.S. Appl. No. 13/052,316, filed Mar. 21, 2011—Pending.
U.S. Appl. No. 13/052,219, filed Mar. 21, 2011—Pending.
U.S. Appl. No. 13/052,200, filed Mar. 21, 2011—Pending.
U.S. Appl. No. 13/246,884, filed Sep. 28, 2011—Pending.
Dielectric Heating with Microwave Energy, Püschner MikrowellenEnergietechnik, pp. 1-4, Jun. 1997.
USP 30-NF25, Disintegration, pp. 276-277, 2007.
Rambali, B., et al., International Journal of Pharmaceutics 220 (2001), pp. 129-140.
Radio Frequency Company, Microwave, (Feb. 19, 2004), pp. 1-2.
International Search Report mailed Aug. 20, 2013 for corresponding Patent Application No. PCT/US2013/039045.
International Search Report mailed Aug. 21, 2013 for corresponding Patent Application No. PCT/US2013/039061.
International Search Report mailed Jun. 8, 2013 for corresponding Patent Application No. PCT/US2013/039047.
Heng, P., et al., Melt Processes for Oral Solid Dosage Forms, Encyclopedia of Pharmaceutical Technology, vol. 4, Jan. 2, 2007, pp. 2257-2261.
International Search Report mailed Nov. 7, 2013 for corresponding Application No. PCT/US2013/039040.
International Search Report mailed Aug. 20, 2031 for Application No. PCT/US2013/039045.
International Search Report mailed Aug. 21, 2013 for Application No. PCT/US2013/039061.
European Search Report mailed Aug. 1, 2013 for Application No. EP08798740.
U.S. Appl. No. 13/718,357, filed Dec. 18, 2012—Pending.
European Search Report mailed Aug. 1, 2013 for Application No. E{08798740.
Maltodextrin (Maltrin M580), Apr. 20, 2000, (PFormulate Excipients).

\* cited by examiner

ORALLY DISINTEGRATIVE DOSAGE FORM

CROSS REFERENCE TO RELATED APPLICATIONS

This is a continuation of prior U.S. application Ser. No. 12/260,151, filed Oct. 29, 2008 now abandoned, which claims the benefit of U.S. Provisional Application 60/983,973 filed on Oct. 31, 2007, which is incorporated by reference herein in its entirety.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved in the oral cavity. Soft tablets that either are chewed or dissolve in the mouth are often employed in the administration of pharmaceuticals where it is impractical to provide a tablet for swallowing whole. With chewable tablets, the act of chewing helps to break up the tablet particles as the tablet disintegrates and may increase the rate of absorption by the digestive tract. Soft tablets are also advantageous where it is desirable to make an active ingredient available topically in the mouth or throat for local effects and/or systemic absorption. Soft tablets are also utilized to improve drug administration in pediatric and geriatric patients. Soft tablets designed to disintegrate in the mouth prior to swallowing are particularly useful for improving compliance of pediatric patients.

It has now been discovered that an orally disintegrating dosage form can be made from a mixture comprising at least one pharmaceutically active agent and at least one hydrated salt. Such process allows for the manufacture of dosage from (such as tablets) without the need of a compression or lyophillization processing step, which in turn, may assist in coated or taste-masked pharmaceutically active agent containing particles remaining intact during the manufacturing process.

SUMMARY OF THE INVENTION

In one aspect, the present invention features an orally disintegrating dosage form including from about 5% to about 40%, by weight, of at least one hydrated salt and a pharmaceutically active agent, wherein the at least hydrated salt has a dehydration temperature of from about 20 to about 120° C.

The present invention also features a process for making an orally disintegrating dosage form including the steps of: a) providing a unit product sheet having a recess in a desired shape and volume suitable for containing said orally disintegrating dosage form; b) introducing into the recess a predetermined amount of a flowable material comprising at least about 5%, by weight, of at least one hydrated salt and a pharmaceutically active agent, wherein said at least one hydrated salt has a dehydration temperature of from about 20 to about 120° C.; c) heating the material in the recess to a temperature above said dehydration temperature for said at least one hydrated salt and for a sufficient period of time to cause the material to fuse into an aggregate, and d) cooling the aggregate in the recess so that the aggregate solidifies into the orally dissolving dosage form suitable for consumption.

The present invention also features a dosage form comprising an edible outer portion and an orally disintegrating portion, the edible outer portion containing the orally disintegrating portion and the orally disintegrating portion including at least about 5%, by weight, of at least one hydrated salt and a pharmaceutically active agent, wherein the at least one hydrated salt has a dehydration temperature of from about 20 to about 120° C.;

The present invention also features a process for making a dosage form comprising an edible outer portion and an orally disintegrating portion including the steps of: a) preparing an edible outer portion having a recess in a desired shape and volume suitable for containing the orally disintegrating portion of said dosage form; b) introducing into the recess a predetermined amount of a flowable material comprising at least about 5%, by weight, of at least one hydrated salt and a pharmaceutically active agent, wherein said at least one hydrated salt has a dehydration temperature of from about 20 to about 120° C.; c) heating the material in the recess to a temperature above said dehydration temperature for said at least one hydrated salt and for a sufficient period of time to cause the material to fuse into an aggregate, and d) cooling the aggregate in the recess so that the aggregate solidifies into the orally dissolving dosage form suitable for consumption.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

Orally Disintegrative Dosage Form

The orally disintegrative dosage form of the present invention includes at least one hydrated salt and a pharmaceutically active agent, and optionally includes one or more carbohydrates, effervescent couples, flavorants, and other ingredients.

In one embodiment, the orally disintegrative dosage form has a hardness of less than about 15 kp/cm$^2$, such as less than 10 kp/cm$^2$, such as less than 5 kp/cm$^2$. In one embodiment a sufficient amount of energy is applied to the orally disintegrative dosage form for a sufficient amount of time to increase its hardness. In one embodiment, energy is applied to the orally disintegrative dosage form in the form of heat or electromagnetic radiation, such as microwaves. Depending on the composition of the disintegrative dosage form, in one embodiment, heating may be performed at a temperature generally in the range of ambient temperature to 100° C. or beyond for a time sufficient to achieve a fusing and/or hardening effect.

In one embodiment, the orally disintegrative dosage form has a friability of less than about 2% (such as less than about 1%, such as less than about 0.5%) following to the application of energy to the flowable material in order to create the disintegrative dosage form, which is the second step of the process. A discussion of orally disintegrative dosage form friability is presented in USP 23 (1995) 1216, p. 1981.

In one embodiment the orally disintegrative dosage form is designed to disintegrate in the mouth when placed on the tongue in less than about 60 seconds, e.g. less than about 45 seconds, e.g. less than about 30 seconds, e.g. less than about 15 seconds.

Hydrated Salt

The orally disintegrating dosage form, or orally disintegrating dosage portion, includes at least one hydrated salt. Examples of hydrated salts include, but are not limited to, sodium sulfate hydrate, sodium carbonate hydrate, calcium chloride hydrate, sodium hydrogen phosphate hydrate, and mixtures thereof. In one embodiment, the hydrated salt has molecular weight from about 150 to about 400 daltons, such as from about 200 to about 350 daltons. In one embodiment, the dosage form/portion comprises from about 5% to about 40%, by weight, of at least one hydrated salt, such as from about 5% to about 20%, by weight.

Carbohydrate

In one embodiment, the orally disintegrating dosage form includes at least 40%, by weight, of at least one carbohydrate. Examples of carbohydrates include, but are not limited to: sugars such as dextrose, dextrose monohydrate, lactose, glucose, fructose, maltodextrin, isomalt, sucrose, corn syrup solids and mannose; carbohydrate alcohols, such as sugar alcohols such as hydrogenated starch hydrolysates such as sorbitol, lactitol, xylitol, erythritol, mannitol, and polyols; and mixtures thereof. In certain embodiments the dosage form comprises at least 40% by weight, such as at least 60% by weight, of at least one carbohydrate.

In one embodiment the weight ratio of said at least one hydrated salt to said at least one carbohydrate is from about 1:4 to about 1:30, such as from about 1:9 to about 1:20.

Water Insoluble Fillers

In one embodiment the orally disintegrating dosage form/portion is substantially free of a directly compressible water insoluble filler. Water insoluble fillers include but are not limited to, microcrystalline cellulose, directly compressible microcrystalline cellulose, celluloses, water insoluble celluloses, starch, cornstarch and modified starches. As described in this embodiment substantially free is less than 2 percent, e.g. less than 1 percent or completely free.

Pharmaceutically Active Agent

The dosage form of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing active ingredients (e.g., aluminum carbonate, aluminum hydroxide, dihydroxyaluminum sodium carbonate, and aluminum phosphate), bicarbonate-containing active ingredients, bismuth-containing active ingredients (e.g., bismuth aluminate, bismuth carbonate, bismuth subcarbonate, bismuth subgallate, and bismuth subnitrate), calcium-containing active ingredients (e.g., calcium carbonate), glycine, magnesium-containing active ingredients (e.g., magaldrate, magnesium aluminosilicates, magnesium carbonate, magnesium glycinate, magnesium hydroxide, magnesium oxide, and magnesium trisilicate), phosphate-containing active ingredients (e.g., aluminum phosphate and calcium phosphate), potassium-containing active ingredients (e.g., potassium bicarbonate), sodium-containing active ingredients (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole and lansoprazole; gastrointestinal cytoprotectives, such as sucralfate and misoprostol; gastrointestinal prokinetics such as prucalopride; antibiotics for H. pylori, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenhydroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, and orphenadrine, methocarbamol; isomers thereof; and pharmaceutically acceptable salts and prodrugs thereof.

Examples of stimulants include, but are not limited to, caffeine.

Examples of sedatives include, but are not limited to sleep aids such as antihistiamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof Examples of anesthetics (e.g., for the treatment of sore throat) include, but are not limited to dyclonene, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent included within the orally disintegrative dosage form is selected from phenylephrine, dextromethorphan, pseudoephedrine, acetaminophen, ibuprofen, ketoprofen, loperamide, famotidine, calcium carbonate, simethicone, and menthol, and pharmaceutically acceptable salts and prodrugs thereof.

In one embodiment, the pharmaceutically active agent is selected from phenylephrine, dextromethorphan, pseudoephedrine, chlorpheniramine, methocarbomal, chlophedianol, ascorbic acid, menthol, pectin, dyclonine, and benzocaine, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (i.e., hydrates) or common organic solvents, and such solvates are also intended to be encompassed within the scope of this invention.

In one embodiment, the pharmaceutically active agent or agents are present in the dosage form in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the dosage form, or may be in the form of particles, which in turn may be coated or uncoated. If the pharmaceutically active agent is in form of particles, the particles (whether coated or uncoated) typically have an average particle size of from about 1 to about 2000 microns. In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

If the pharmaceutically active agent has an objectionable taste, the pharmaceutically active agent may be coated with a taste masking coating, as known in the art. Examples of suitable taste masking coatings are described in U.S. Pat. Nos. 4,851,226, 5,075,114, and 5,489,436. Commercially available taste masked pharmaceutically active agents may also be employed. For example, acetaminophen particles, which are encapsulated with ethylcellulose or other polymers by a coacervation process, may be used in the present invention. Coaccervation-encapsulated acetaminophen may be purchased commercially from Eurand America, Inc. (Vandalia, Ohio) or from Circa Inc. (Dayton, Ohio).

The pharmaceutically active agent may be present in pure crystal form or in a granulated form prior to the addition of the taste masking coating. Granulation techniques may be used to improve the flow characteristics or particle size of the pharmaceutically active agents to make it more suitable for compression or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation, the details of which are disclosed in, "The Theory and Practice of Industrial Pharmacy, $3^{rd}$ edition", Chapter 11, Lachman, Leon et. al, 1986.

As discussed above, one advantage of the orally disintegrating dosage form/portion described herein is the ability to incorporate modified particles containing a pharmaceutically active agent, such as taste-masked particles, coated granules, or coated beads which are typically sensitive to compression forces during manufacture. Traditional tablet compression can subject coated particles to forces, which can compromise the function of the coating (e.g., modify taste-masking or modified release properties). In one embodiment the orally disintegrating form of this invention incorporates gel-coated liquid filled beads, which may contain a flavorant, an active ingredient or mixtures thereof. In one embodiment the gel-filled beads are coated with materials that include, but not limited to, hydrocolloids (such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof) and a plasticizer (such as propylene glycol, glycerin or mixtures thereof). Since, in one embodiment, the dosage form disclosed herein does not undergo a compression step, the gel-coated liquid filled beads are less likely break.

In one embodiment, the orally disintegrative dosage form/portion incorporates modified release coated particles (i.e., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, extended release or delayed release. In general, modified release dosage forms are formulated to make the active agents(s) available over an extended period of time after ingestion, which thereby allows for a reduction in dosing frequency compared to the dosing of the same active agent(s) in a conventional dosage form. Modified release dosage forms also permit the use of active agent combinations wherein the duration of one active ingredient may differ from the duration of another active ingredient. In one embodiment the dosage form contains one pharmaceutically active agent that is released in an immediate release manner and an additional active agent or a second portion of the same active agent as the first that is modified release.

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent.

In one embodiment one or more active ingredients or a portion of the pharmaceutically active agent may be bound to an ion exchange resin for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the orally disintegrative dosage form meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

Effervescent Couple

In one embodiment, the orally disintegrative dosage form further includes one or more effervescent couples. In one embodiment, effervescent couple includes one member from the group consisting of sodium bicarbonate, potassium bicarbonate, calcium carbonate, magnesium carbonate, sodium carbonate and one member selected from the group consisting of citric acid, malic acid, fumaric acid, tartaric acid, phosphoric acid, alginic acid.

In one embodiment, the combined amount of the effervescent couple(s) in the orally disintegrative dosage form is from about 0.1 to about 20 percent by weight, such as from about 2 to about 10 percent by weight of the total weight of the disintegrative dosage form.

Other Ingredients

The orally disintegrative dosage form may include other conventional ingredients, including other fillers, dry binders like polyvinyl pyrrolidone and the like; sweeteners such as aspartame, acesulfame potassium, sucralose, and saccharin; lubricants, such as magnesium stearate, stearic acid, talc, and waxes; preservatives; flavors; disintegrants, antioxidants; acidulants, such as but not limited to citric acid, malic acid, tartaric acid, ascorbic acid, and fumaric acid; surfactants; superdisintegrants; flavor and aroma agents; antioxidants; preservatives; texture enheancers; and coloring agents.

Examples of suitable sweeteners for use in the dosage form include, but are not limited to, synthetic or natural sugars, sucralose, saccarin, sodium saccarin, aspartame, acesulfame K or acesulfame, potassium acesulfame, thaumatin, glycyrrhizin, dihydrochalcone, alitame, miraculin, monellin, stevside, and mixtures thereof.

Examples of superdisintegrants include but are not limited to croscarmellose sodium, sodium starch glycolate and cross-linked povidone (crospovidone). In one embodiment the orally disintegrative form/portion comprises up to about 5% by weight of such superdisintegrant.

Examples of suitable flavor and aroma agents include, but are not limited to, essential oils including distillations, solvent extractions, or cold expressions of chopped flowers, leaves, peel or pulped whole fruit comprising mixtures of alcohols, esters, aldehydes and lactones; essences including either diluted solutions of essential oils, or mixtures of synthetic chemicals blended to match the natural flavour of the fruit (e.g., strawberry, raspberry and black currant); artificial and natural flavors of brews and liquors (e.g., cognac, whisky, rum, gin, sherry, port, and wine); tobacco, coffee, tea, cocoa, and mint; fruit juices including expelled juice from washed, scrubbed fruits such as lemon, orange, and lime; mint; ginger; cinnamon; cacoe/cocoa; vanilla; liquorice; menthol; eucalyptus; aniseeds nuts (e.g., peanuts, coconuts, hazelnuts, chestnuts, walnuts, and colanuts); almonds; raisins; and powder, flour, or vegetable material parts including tobacco plant parts (e.g., the genus Nicotiana in amounts not contributing significantly to a level of therapeutic nicotine).

Examples of antioxidants include, but are not limited to, tocopherols, ascorbic acid, sodium pyrosulfite, butylhydroxytoluene, butylated hydroxyanisole, edetic acid, and edetate salts. Examples of preservatives include, but are not limited to, citric acid, tartaric acid, lactic acid, malic acid, acetic acid, benzoic acid, and sorbic acid.

Examples of texture enhancers include, but are not limited to, pectin, polyethylene oxide, and carageenan. In one embodiment, texture enhancers are used at levels of from about 0.1% to about 10% percent by weight.

Disintegration Test

In one embodiment the orally disintegrating dosage form/portion meets the criteria for Orally Disintegrating Tablets as defined by the draft Food and Drug Administration guidance, as published in April 2007, incorporated herein by reference. In one embodiment the orally disintegrating dosage form/portion of this invention meets a two-fold definition for orally disintegrating tablets including the following criteria: 1) that the solid dosage form is one which contains medicinal substances and which disintegrates rapidly, usually within a matter of seconds, when placed upon the tongue and 2) be considered a solid oral preparation that disintegrates rapidly in the oral cavity, with an in-vitro disintegration time of approximately 30 seconds or less, when based on the United States Pharmacopeia (USP) disintegration test method for the specific medicinal substance or substances.

To determine the in-vitro disintegration for the dosage form, the disintegration test for "Uncoated Tablets" according to USP30-NF25 (using water as the immersion fluid) should be used. Briefly, one dosage unit is placed in each of the six tubes of the basket, and water (maintained at 37±2 C) is used as the immersion fluid. The disintegration time is determined by taking the greatest of six measurements of the time period required to completely disintegrate the respective dosage form/portion. In one embodiment, the in-vitro disintegration time of the orally disintegrative dosage form/portion is less than about 30 seconds, such as less than about 15 seconds.

In the embodiment wherein the orally disintegrative inner portion is combined with an edible outer portion, the in-vitro disintegration time of the outer edible outer portion is at least ten times, such as at least 50 times or at least 100 times longer than the disintegration time of the orally disintegrative portion.

Hardness Test

Hardness is a term used in the art to describe the diametral breaking strength as measured by a Schleuniger Hardness Tester as described in Leiberman et al., Pharmaceutical Dosage Forms—Tablets, Volume 2, 2nd ed., Marcel Dekker Inc., 1990, pp. 213-217, 327-329. In order to perform the hardness test, a single dosage form/portion is placed into the steel chamber within the hardness tester, and the steel piston pushes against the dosage form until it breaks, measuring the force applied as a hardness measurement. In general, 5 dosage forms/portions are tested from any one sample in order to provide a mean hardness value in kiloponds. In one embodiment the dosage form has a hardness of less than 5 kp/cm$^3$, such as less than 2 kp/cm$^3$, such as less than 1.5 kp/cm$^3$.

An additional test for hardness of an orally disintegrating dosage form/portion of the present invention relies upon a Texture Analyser TA-XT2i that is fitted with a 7 millimeter diameter flat faced probe and setup to measure and report compression force in grams. The probe moves at 0.5 millimeters per second to a depth of penetration of 2 millimeters. The maximum compression force is recorded. In one embodiment, the measured forces recorded for orally disintegrative dosage forms/portions made in accordance with the present invention preferably ranges from approximately 700 grams to about 6000 grams, up to at most 10,000 grams.

In one embodiment the flowable material (e.g., the powder) is tamped slightly prior to the heating step. As the particle size of the hydrate is decreased following the tamping, less heat is needed to fuse the agglomerate to achieve the same hardness.

Manufacture and Packaging of Orally Disintegrative Dosage Form (a) Unit Product Sheet Pharmaceutical dosage forms, such as pills, capsules, tablets and the like, may be packaged in unit product sheets, such as blister packages. In one embodiment, the blister package are comprised of multi-layered sheets of material having pockets for containing the dosage forms. Conventional blister packages include packages having a foil layer through which a user of the package must push the tablet, breaking the foil. U.S. Pat. No. 4,158,411 discusses such a blister package. Blisters having open tops for containing pharmaceutical tablets are formed in a flexible sheet of plastic or aluminum material. An optional paperboard layer having disc-shaped punch-outs covers the open tops of the blisters overlying each dosage form. A foil layer covers the paperboard layer, holding the punch-outs in place. To open the package, the user must collapse the blister and push the tablet through the foil, also removing the punch-outs.

Another type of blister package provides perforations between separable blister units so that the user can separate an individual dosage from the package prior to opening. U.S. Pat. No. 4,398,634 illustrates a blister package of this type. The blister portions are defined by tear-resistant, substantially planar plastic sheets sealed to one another in seal zones. The seal zones are located around the periphery of each blister unit, forming pockets of unsealed areas which define the blisters, centrally located in the blister unit. Weakened areas in the seal zones allow the user to separate the blisters into individual units by tearing a unit away from the package. Upon separation of the unit, the user tears through the plastic layers, through the blister, to gain access to the dosage form. A slit in the corner of the unit is provided for easy tearing.

Another type of blister package includes individual units that, upon separation, reveal a tab for opening the blister. U.S. Pat. No. 5,046,618 discloses this type of blister package. The blister package is formed from a sheet of material having blisters formed therein and a substantially planar lidding sheet. This blister package has two rows of blisters, each blister unit separated from an adjacent unit by perforations. Tear strips separate the rows with perforations that run between the tear strips and the blister units. To open the package, a user separates an individual unit from the package with a tear strip still attached to the unit. This tear strip must be removed to access the tab, which comprises an unsealed area on the corner of the blister unit. After the tear strip is removed, the user grabs the corner of the lidding sheet and peels the sheet back to reveal the dosage form. Suitable materials for constructing the blister cavity for use in the invention described herein include, but are not limited to, polyvinyl chloride (PVC), polyvinylidene chloride (PVDC), aluminum, and polychlorotrifluoroethylene (PCTFE).

There are various production based machines which may be suitable for making blister packaging, including the use of platen sealing such as that made by the Uhlmann Packaging Systems company under model number UPS4 and the use of rotary sealing such as that made by the Bosch Packaging Group company in Minneapolis, Minn., USA. under model number TLT 1400 and the TLT 2800.

The unit product sheet may be comprised of a sheet having one or a plurality of recesses (such as from about 2 to about 12, such as from about 2 to about 6) containing dosage forms arranged, for example, in rows and columns. The unit product sheet may includes a plurality of unit packages, each unit package incorporating one recess and a sheet overlying that recess. A set of tear lines can be included between the adjacent unit packages so that a user of the package may tear along the tear lines to separate a unit package.

The recesses of the package and the dosage forms disposed in the recesses may have essentially any shape. For example, the dosage forms may be disk-shaped tablets, oblong capsules, square-shaped pills, hemispheres or truncated cones. Shapes for recesses include circular, oblong, polygonal, triangles or star shapes in the plane of the blister sheet.

Furthermore, the walls and bottom of the recesses may define a shape in the form of a surface of revolution, about a vertical axis normal to the flange surrounding each of the recesses. For example, the recesses may have a curved, cup-like shape. Where the dosage forms are disc-shaped, they may each have an edge which contacts the walls of the recess in which each dosage form is disposed. The edge and walls define an annular region of contact coaxial with the vertical axis of the recess. The edge of such a disc-shaped dosage form may comprise a bevel, which contacts the walls of the recess. The annular region of contact prevents shifting of the dosage form within the blister and the damage to the dosage form associated with such shifting. The unit product sheet must be substantially deformable to allow for the punch out and removal of the orally disintegrating dosage form without breakage of the dosage form. The shape of the unit product sheet must also be such that the orally disintegrating dosage form can be punched out and removed without breakage of the dosage form. In one embodiment the (obtuse) angle of the bottom face of the blister to the angle of the side wall of the blister is greater than 90° C., e.g. greater than 110° C.

(b) Manufacture within Unit Product Sheets

The orally disintegrative dosage form may be made in a variety of methods. In one embodiment, the orally disintegrating dosage form is made by a method comprising the steps of: (a) providing a unit product sheet having at least one recess in a desired shape and volume suitable for containing the resulting orally disintegrating dosage form; (b) introducing into the recess a predetermined amount of a flowable material comprising at least about 5%, by weight, of at least one hydrated salt and a pharmaceutically active agent, wherein said at least one hydrated salt has a dehydration temperature of from about 20 to about 120° C.; (c) optionally, sealing the flowable material within the recess; (d) heating the material in the recess to a temperature above said dehydration temperature for said at least one hydrated salt and for a sufficient period of time to cause the material to fuse into an aggregate, and (e) cooling the aggregate in the recess so that the aggregate solidifies into the orally dissolving dosage form suitable for consumption.

In one embodiment a lubricant is added to the unit product sheet (e.g., a blister package) prior to the addition of the flowable material. This lubricant may be a liquid or solid, or integrated into the unit product sheet material. Suitable lubricants include but are not limited to solid lubricants such as magnesium stearate, starch, calcium stearate, aluminum stearate, talc, hydrogenated vegetable oil, sodium stearyl fumarate, glyceryl behenate, and stearic acid; or liquid lubricants such as but not limited to simethicone, lecithin, vegetable oil, olive oil, or mineral oil. In certain embodiments the lubricant is added at a percentage by weight of the orally disintegrating dosage form of less than 5 percent, e.g. less than 2 percent, e.g. less than 0.5 percent.

A flowable material, preferably in the form of a solid such as a powder or particulate agglomerate, is introduced into at least one of the recesses in the unit product sheet. In one embodiment the flowable material can be defined as one with an angle of repose of 20 to 44 degrees. The angle of repose is defined by Terzaghi in "The Theoretical Soil Mechanics in Engineering Practice", Wiley, N.Y., 1948, as the angle between the horizontal and slope of a heap of soil (or powder) dropped from some elevation. In the embodiments of this invention it is defined as the constant angle to the horizontal assumed by a cone like pile of material. This pile is built from a point above the horizontal using two flat glass plates separated by at least ½ inch and which allows for overflow.

The flowable material is preferably introduced into recesses that are provided in product holding tray that can be a blister-type package described above. The materials in each unit are heated to a temperature above the dehydration temperature for the at least one hydrated salt and for a sufficient period of time to cause the material to fuse into an aggregate, and resulting in a unitary dosage form suitable for handling, removal from the recess of the unit product sheet (such as a blister) and ingestion. In one embodiment, the other components remain solid and maintain their physical properties, including hardness (e.g., the temperature of the recess contents during the heating step should be above the dehydration temperature, but below the melting points and the decomposition temperatures of the other ingredients of the dosage form, including the pharmaceutically active agent). The time of heating is dependent on the at least one hydrated salt and the dimensions of the orally disintegrating form or portion, and must be sufficient in conjunction with the temperature to fuse and stabilize the agglomerate form. In certain cases the active ingredient may be temperature sensitive, requiring different minimal heating temperature with a longer heating time.

Suitable heat sources include a radiant heater, conductive heating, convective heating, radiofrequency heating, sonic heating, microwave heating, or laser. In one embodiment, the temperature and time of cooling are such as to bridge the carbohydrate or carbohydrate granules with the hydrate salt, creating a solidified dosage form. In one embodiment, a portion of the carbohydrate (e.g., carbohydrate granules) dissolves under release of the water from the hydrated salt and then, upon recrystallization, forms bridged crystalline structures at a microscopic level. In one embodiment, the temperature during cooling is about 25° C. to about 0° C., and the time of cooling is about 10 to about 60 seconds. Generally, the higher the temperature during cooling, the longer the cooling time. In one embodiment the cooling takes place at room temperature (25° C.) for greater than 5 minutes.

(c) Manufacture within an Edible Outer Portion

The orally disintegrating dosage form may also be incorporated within a separate edible outer portion, such as a hard candy. In one embodiment, the hard candy portion is a sugar glass hard candy formed from by cooling boiled sugar candy. In another embodiment, the hard candy portion is a compressed sugar candy made by compression, with a hardness of at least 15 kiloponds, such as at least 20 kiloponds. In one embodiment, an edible outer portion is pre-made prior to the addition of the orally disintegrating dosage form. In one such embodiment, an outer hard candy or compressed candy ring is manufactured as an edible outer portion, the fixed amount of flowable material containing at least one active ingredient is added, and the dosage form is heated for the temperatures and times described above to form an orally disintegrating tablet portion within the dosage form, and subsequently packaged into a blister, pouch or bottle. In one embodiment, the edible outer portion is substantially enclosed in order to hold the material for the heating or fusing step. In these embodiments, substantially enclosed can be achieved by forming a ring, an oval or other shape such as but not limited to a triangle, star, moon, etc. with an internal hollow portion sufficient to hold the material. This form is placed onto a surface in order to hold the material. This surface may be suitable for holding any flat shape including but not limited to plastic, metal, or composite. This may also be achieved within a preformed unit product sheet and may have negative embossing in order to transfer a logo, image or product identification upon heating and fusing of the dosage form. Alternatively, the dosage form may be lasered or printed for aesthetic imaging (shapes, characters, colors, etc.) or identification (product name, dosage, etc.).

In one embodiment, the outer hard candy form is made using uniplast rolling, roping and subsequent cutting and stamping, as well as depositing into molds. In one embodiment, the hard candy portion contains one or more sugars selected from the group consisting of isomalt, sucrose, dextrose, corn syrup, lactitol, and hydrogenated starch hydrolysates. In one embodiment, the hard candy portion contains at least 50% (such as at least 75%, such as at least 90%) by weight of such sugar(s).

In one embodiment, the dosage form comprising an edible outer portion and an inner orally disintegrating portion is coated with an immediate release sugar coating or film coating. To produce such a dosage form, the step following the fusing (heating) and subsequent cooling of the dosage form would involve further sugar or film coating in a coating pan.

In one embodiment the edible outer portion contains a pharmaceutically active agent and the orally disintegrating portion contains the same pharmaceutically active agent. In one embodiment the edible outer portion contains a pharmaceutically active agent and the orally disintegrating dosage form contains a different pharmaceutically active agent. In one embodiment the edible outer portion disintegrates at a rate of at least 10 times greater than the rate of the orally disintegrating dosage form portion, such as at least 20 times greater. In one embodiment, the orally disintegrating portion meets the FDA requirements for Orally Disintegrating Tablets. In one embodiment the orally disintegrating portion contains an upper respiratory pharmaceutically active agent such as pseudoephedrine, dextromethorphan, cetirizine, diphenhydramine, and chlorpheniramine and the edible outer portion contains menthol.

Use of Orally Disintegrative Dosage Form

In one embodiment, the present invention features a method of treating an ailment, the method comprising orally administering the above described dosage form wherein the dosage form includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratidine, fexofenadine, diphenhydramine, dextromethorphan, chlorpheniramine, chlorphedianol, and pseudoephedrine.

EXAMPLES

Specific embodiments of the present invention are illustrated by way of the following examples. This invention is not confined to the specific limitations set forth in these examples.

Example 1

Orally Disintegrating Immediate Release Loratidine Tablet Blend (a) Cold Forming of Blister Packaging Using a Bosch TLT 1400 (rotary thermoforming sealing) blister line machine, a web of aluminum blister forming material is unwound from a roll, and then indexed into the forming station where compressed air and/or a vacuum is used to form cavities in the web at a ⅝ inch flat round cavity with depressions containing the product's tradename as an identifier to produce a thermoformed web.

The resulting thermoformed web is indexed into a feeder station where the tablet blend formulation described below in Example 2 are deposited into the formed cavities.

(b) Tablet Blend Formulation

An orally disintegrating immediate release loratidine tablet blend formulation including the ingredients of Table 1 is manufactured as follows:

TABLE 1

| Granulation Blend | G/Batch | Mg/Tablet |
|---|---|---|
| Dextrose Monohydrate | 87.71 | 1052.5 |
| Sodium Hydrogen Phosphate Hydrate* | 9.74 | 116.9 |
| Sucralose USP | 0.60 | 7.2 |
| Flavor | 1.12 | 13.4 |
| Loratidine | 0.83 | 10.0 |
| Total | 100.0 | 1200.0 |

*Chemical formula: $Na_2HPO_4 \cdot 7H_2O$

Dextrose Monohydrate, sucralose and flavor are screened through a 30 mesh screen and placed into a 500 cc plastic bottle and mixed end-over-end for 5 minutes. The loratidine and sodium hydrogen phosphate hydrate are added and blended end over end for an additional 3 minutes. The blend is then filled into the pre-formed blister cavities in Example 1.

(c) Packaging of Blisters

Blister forming pins or punches, used to pre-form the blister cavities prior to addition of the flowable material, contain small injection ports which inject approximately about 0.1-5 mg of soy lecithin onto the surface of the blister upon forming the cavity, in order to facilitate ejection of the blend formulation. The formed blister material from Example 1 is then indexed into a seal station where a foil lidding is applied. The lidding material is unwound from a roll and sealed together using heat and mechanical pressure resulting in the product being contained within the cavity. The sealed blister is placed into a convection oven set at 55° C. for 15 minutes The sealed web is indexed toward the perforating station. The perforating station uses sharp cutting blades to place perforations through the web resulting in a blister card with an opening feature. Lastly, the web moves to the punch station where individual blister are cut from the web into individual cards containing 6 orally disintegrating forms per card.

The blister cavity is then cooled at 0° C. for 5 minutes and sealed. The tablets are then removed from the blister cavity as a single dosage unit for ingestion.

Example 2

Preparation of Outer Edible Ring Portion with Fused Orally Disintegrating Tablet Inner Portion (a) Preparation of an Edible Outer Ring Portion All materials set forth in Table 2 below are manually passed through a 30 mesh screen. One and a half (1.5) kg of the resulting blend are placed in a 4 quart V-Blender and mixed for 5 minutes.

TABLE 2

| Ingredients | Weight Percent (w/w) | Weight (mg) |
|---|---|---|
| Sorbitol | 5 | 50 |
| Compressible Sucrose* | 92.75 | 927.5 |
| Menthol | 1 | 10 |
| Peppermint Flavor | 0.5 | 5 |
| Magnesium Stearate | 0.75 | 7.5 |
| TOTAL | 100 | 1000 |

*Commercially available from Domino Specialty Ingredients, Baltimore, MD

Four hundred (400) g of the resulting blend is then removed from the blender and compressed on a rotary tablet press at 60 rpm using ¾" ringed tablet tooling in order to yield flat faced rings having ½" empty centers and having a weight of 1000 mg and a hardness range of not less than 15 kp/cm², and a thickness of about 0.20 inches.

(b) Preparation of Inner Orally Disintegrating Portion

An orally disintegrating immediate release loratidine tablet blend formulation including the ingredients of Table 3 is manufactured as follows:

TABLE 3

| Granulation Blend | G/Batch | Mg/Tablet |
|---|---|---|
| Dextrose Monohydrate | 86.67 | 433.3 |
| Sodium Hydrogen Phosphate Hydrate* | 9.62 | 48.1 |
| Sucralose USP | 0.6 | 3 |
| Flavor | 1.12 | 5.6 |
| Loratidine | 2 | 10 |
| Total | 100 | 500 |

*$Na_2HPO_4 \cdot 7H_2O$

Dextrose Monohydrate, sucralose and flavor are screened through a 30 mesh screen and placed into a 500 cc plastic bottle and mixed end-over-end for 5 minutes. The loratidine and sodium hydrogen phosphate hydrate are added and blended end over end for an additional 3 minutes.

(c) Preparation of Edible Outer Ring Portion with Fused Orally Disintegrating Tablet Inner Portion The edible outer ring portion from part (a) is placed into a formed blister cavity. 500 mg of the blend from part (b) is then filled into hole in the ring, and the blister is sealed. The sealed blister is placed into a Convection Oven set at 55° C. for 15 minutes. The blister cavity is then cooled at 0° C. for 5 minutes. The dosage forms are then removed from the blister cavity as a single dosage unit for ingestion.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A process for making a dosage form comprising:
    a) introducing a flowable powder material into a recess, said flowable material comprising (i) at least about 5% by weight, of at least one hydrated salt and (ii) a pharmaceutically active agent, wherein said at least one hydrated salt has a dehydration temperature of from about 20 to about 120° C.;
    b) heating the flowable powder material in the recess to a temperature above said dehydration temperature for said at least one hydrated salt and for a sufficient period of time to cause the flowable powder material to fuse into an aggregate, wherein said heating is applied via radiofrequency heating; and
    c) cooling the aggregate in the recess so that the aggregate solidifies into said dosage form; wherein said dosage form disintegrates in the mouth when placed on the tongue in less than about 60 seconds.

2. A process of claim 1, wherein said at least one hydrated salt is selected from the group consisting of sodium sulfate hydrate, sodium carbonate hydrate, calcium chloride hydrate, sodium hydrogen phosphate hydrate, and mixtures thereof.

3. The process of claim 1, wherein the dosage form comprises from about 5% to about 40%, by weight, of at least one hydrated salt.

4. The process of claim 1, wherein said flowable material further comprises at least one carbohydrate.

5. The process of claim 4, wherein at least one of said at least one carbohydrate is selected from the group consisting of dextrose, dextrose monohydrate, lactose, glucose, fructose, isomalt, sucrose, mannose, maltose, maltodextrin, corn syrup solids, hydrogenated starch hydrolysates, lactitol, xylitol, mannitol, erythritol, and sorbitol, and mixtures thereof.

6. The process of claim 4, wherein at least one of said at least carbohydrate is dextrose monohydrate.

7. The process of claim 4, wherein said dosage form comprises at least 40% of said at least one carbohydrate.

8. The process of claim 4, wherein the weight ratio of said at least one hydrated salt to said at least one carbohydrate is from about 1:4 to about 1:30.

9. The process of claim 1, wherein said flowable material is tamped in said recess prior to heating.

10. The process of claim 1, wherein said dosage form has an in vitro disintegration time of approximately 30 seconds or less based on the United States Pharmacopeia (USP) disintegration test method for the specific medicinal substance or substances.

11. The process of claim 1, wherein said dosage form meets the criteria for Orally Disintegrating tablets as defined by the draft Food & Drug Administration guidance, as published April, 2007.

12. The process of claim 1, wherein said dosage form has a hardness of from about 700 to about 6000 grams as measured using Texture Analyzer TA-XT2i that is fitted with a 7 millimeter diameter flat faced probe.

13. The process of claim 1, wherein said dosage form has a hardness of less than 5 kp/cm³.

14. The process of claim 1, wherein the recess is a blister-type package.

15. The process of claim 1, wherein said cooling takes place at room temperature.

16. A dosage form made by the process of claim 1.

17. The dosage form of claim 16, wherein said flowable material further comprises at least one carbohydrate.

* * * * *